United States Patent [19]

McNally et al.

[11] Patent Number: 5,089,298
[45] Date of Patent: Feb. 18, 1992

[54] SYNERGISTIC EFFECT OF AMYLOPECTIN-PERMETHRIN IN COMBINATION ON TEXTILE FABRICS

[75] Inventors: Bartley F. McNally, North Providence, R.I.; Richard F. Lacerte, Hudson, Mass.

[73] Assignee: The United States of America as represented by the Secretary of the Army, Washington, D.C.

[21] Appl. No.: 617,721

[22] Filed: Nov. 19, 1990

[51] Int. Cl.$^5$ .......... B05D 3/12; B05D 1/18; B05D 1/38; B05D 7/24

[52] U.S. Cl. .................. 427/240; 427/242; 427/322; 427/324; 427/370; 427/417; 427/430.1; 427/439

[58] Field of Search ............ 427/430.1, 439, 314–316, 427/322, 324, 240, 242, 370, 417; 8/490

[56] References Cited

U.S. PATENT DOCUMENTS 4,503,100  3/1985  de Sousa et al. ............ 427/428
4,666,747  5/1987  Quinn ............ 106/15.05 X

*Primary Examiner*—Evan Lawrence
*Attorney, Agent, or Firm*—Richard J. Donahue

[57] ABSTRACT

The invention relates to the impregnation of clothing, specifically Battle Dress Uniforms (BDUs) used by the U.S. Military, with amylopectin fabric wrinkle inhibitor and permethrin insect/arthropod repellent in combination. In one disclosed embodiment of the invention, BDUs are loaded into a field laundry, are rinsed with clear water at 120 degrees Fahrenheit, and amylopectin is applied at a particular concentration. The BDUs preferably are then steam pressed. Permethrin at a predetermined concentration is then applied preferably by the "Individual Dynamic Absorption Application" (IDAA) procedure. The retention of permethrin by clothing treated with amylopectin unexpectedly reveals a substantially higher retention level than clothing without treatment by amylopectin after multiple laundry cycles, providing thereby a dramatic improvement in the insect/arthropod repelling action of the clothing over time.

8 Claims, 1 Drawing Sheet

SYNERGISTIC EFFECT OF AMYLOPECTIN-PERMETHRIN IN COMBINATION ON TEXTILE FABRICS

STATEMENT OF GOVERNMENT USE

The invention described herein may be manufactured, used, and licensed by or for the Government for Governmental purposes without the payment to us of any royalty thereon.

BACKGROUND OF THE INVENTION

1. Field of the Invention

The invention relates to the field of insect and arthropod repellents, and more particularly, to the impregnation of textile fabrics with amylopectin and Permethrin in combination therewith.

2. Description of the Prior Art

Permethrin and amylopectin are derived from chrysanthemum flowers, yet no prior art has revealed or provided a motivation for applying these in combination to textile fabrics.

A synthetic pyrethroid, Permethrin is known for its insect/arthropod repellent qualities, in addition to its relative safety when used by humans. Permethrin is typically used by spray application. Thus, caution must be exercised because Permethrin is known to poison fish if it is introduced inadvertently into a stream or water cycle. Clothing may be sprayed with Permethrin in a closed environment, though this is not an economical manner of application, since only about forty percent of the Permethrin may actually adhere to the clothing. Nor is there any known manner of guaranteeing that the Permethrin will be retained by the clothing during washing cycles, or, for that matter, during ordinary wear.

The continuous use of starch at higher concentrations than 0.75% on U.S. Military Battle Dress Uniforms (BDUs) is generally a prohibited practice in view of the consequent shortening of the durable life of the BDUs.

Amylopectin, a water soluble form of starch, is a known fabric wrinkle inhibitor.

SUMMARY OF THE INVENTION

The present invention provides a method of impregnating clothes, specifically Battle Dress Uniforms (BDUs), with amylopectin and Permethrin in combination, which has been found to synergistically provide greater retention of Permethrin through a substantially greater number of laundering cycles than BDUs having Permethrin alone. Moreover, the invention provides a method of application of the Permethrin and amylopectin that is at once safe, efficient, convenient, cost-effective, and environmentally sound.

Although the applications of amylopectin and Permethrin to BDUs or other textiles may take place in any order, it is presently preferred to first apply the amylopectin and then to apply the Permethrin to the BDUs. In accord therewith, BDU trousers and coats, for example, are loaded into laundry machines, and rinsed. While thus wetted, amylopectin, which is water soluble, is applied by mixing a predetermined amount thereof in liquid phase to the rinse water. In further accord therewith, the water is then extracted, preferably by spinning the BDUs at high speed, and the water-extracted BDUs may then be steam-pressed to further extract any remaining fluid. Although this step is preferred, it is not believed to be necessary to provide the quite remarkable synergistic effects of enhanced Permethrin retention provided by the present invention. In further accord with the present invention, the BDUs are then rolled up, and are inserted into a bag. Thus contained, and in accordance with a U.S. Army procedure referred to as the Individual Dynamic Absorption Application (IDAA) procedure, a predetermined amount of Permethrin is added to the bag, which is then sealed to prevent escape of volatile components into the environment. The amount is determined such that all of the Permethrin solution is absorbed. The BDUs are allowed to soak in the Permethrin solution and absorb it through a wicking action. Thereafter, the BDUs are removed and allowed to dry preferably in air.

The invention results in substantially higher retention levels of Permethrin in BDUs through a substantial number of laundering cycles than previously possible.

DETAILED DESCRIPTION OF THE DRAWINGS

A more complete understanding of the present invention and the attendant advantages and features thereof will be more readily understood by reference to the following detailed description thereof when considered in conjunction with the accompanying drawings wherein.

DETAILED DESCRIPTION OF THE PREFERRED EMBODIMENTS

Figure 1:
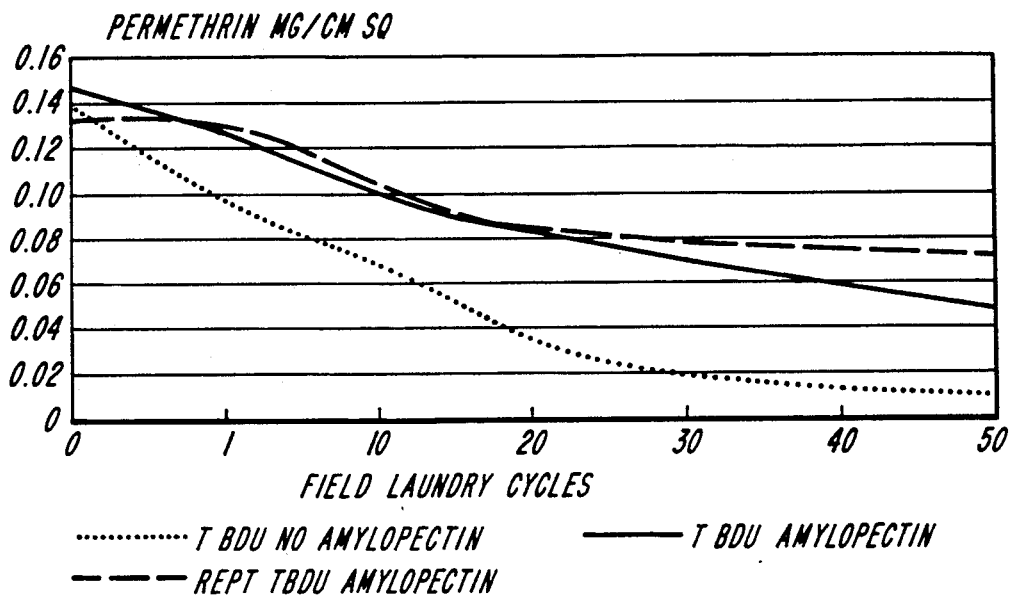
FIG. 1 is a graph showing Permethrin retention in Temperate (nylon/cotton) Bttle Dress Uniforms in combination with amylopectin and without amylopectin.

When the procedure for treating Battle Dress Uniforms (BDUs) with amylopectin and Permethrin is applied in accordance with an exemplary method of the invention, the treated BDUs, even after fifty (50) laundry cycles, have been found to retain an integral multiple of the amount of Permethrin than BDUs which are not treated with amylopectin. The steps described herein may be viewed as best adapted to the needs of military personnel, but the invention is not limited thereto. The synergistic effects of the markedly improved and quite unexpected retention of Permethrin, and therewith of enhanced insect/anthropod repellent action which is sustained over multiple washing cycles, may be otherwise achieved so long as both a starch, such as amylopectin, and Permethrin, are conjointly applied to textiles, such as BDUs, to be treated in order to exhibit the enhanced insect/anthropod repellent action which is an objective of the present invention.

In a presently preferred embodiment, BDUs, a coat and trousers, for example, are loaded into a laundry machine, such as a field laundry machine, and are rinsed with clear water, preferably at 120 degrees Fahrenheit, for thirty (30) seconds.

Any kind of BDUs may be treated by the present invention, which bestows advantages where different clothing is used depending on the climate. BDUs made of nylon and cotton material are referred to as Temperate BDUs, because they can be used in cooler weather. Hot weather BDUs, on the other hand, are worn in hot weather and tend to be made of cotton only. Both kinds of BDUs may be treated by the processes of the present invention. BDUs that are not new should be washed with any standard detergent prior to rinsing, and preferably with detergents having low or zero bleach contents.

Amylopectin, preferably in a 0.75 concentration, is then added to the rinse water, preferably for five minutes at 120 degrees Fahrenheit.

Water is then extracted from the BDUs, preferably by centrifuging. Such centrifuging may be done through the spin cycle of the laundry machine, or by removing the BDUs from the field laundry and placing them in a centrifuge. Preferably, the water-extracted BDUs are then steam-pressed dry, although this step is not believed to be necessary.

It is not advisable to add Permethrin to the laundry cycle, since such an application of Permethrin into the machine would constitute a waste of the Permethrin and, more important, could create a potentially dangerous effluent that might find its way to a stream or other places inhabited by fish.

The Permethrin is preferably added to the amylopectin treated BDUs in accordance with a method used by the U.S. Army and referred to as the Individual Dynamic Absorption Application (IDAA) procedure. The IDAA is a field method for applying chemicals such as Permethrin to BDUs without contaminating the environment. The method enables military personnel, at any given military site, for example, to treat their own BDUs with relatively simple equipment and in emergency situations. In accordance with this method, the BDUs, which have been water-extracted, preferably steam-pressed, and amylopectin-treated, are then tightly rolled and placed into a water impermeable bag, such as a sealable Plastic bag. Permethrin, preferably in a concentration of 40 solid, together with an effective amount of water, is thereafter poured into the bag. The bag is sealed and then shaken to distribute the Permethrin/water mixture, which is then absorbed by the BDUs through wicking action.

It is desirable to ascertain the maximum absorption for any particular roll of clothing placed into the bag, so that the volume of Permethrin solution poured into the bag is less than the known maximum absorption volume. This may be done by taking an identical rolled set of clothes and measuring how much water is absorbed without excess drippage. If it is known that a particular BDU will absorb 500 milliliters of Permethrin solution, then 350 milliliters of Permethrin solution can be used safely, for example, without waste of Permethrin or permitting contamination of the environment.

This predetermined amount of Permethrin in the preferred embodiment of the invention, is added to the bag in such concentration that for every square centimeter of clothing 0.125 mg. of Permethrin is available to be absorbed. This amount has been approved by the U.S. Army Medical Department in the context of spray applications. A wide range of Permethrin concentrations, however, may be used. Beyond 0.125 mg. Permethrin per square centimeter of fabric, however, there are diminishing returns insofar as the efficacy of Permethrin retained by the BDUs does not increase in direct proportion to the amount of Permethrin used.

After all of the Permethrin has been absorbed, typically about a two hour time interval will have elapsed, and the bag is opened. The BDUs are removed and allowed to dry in air.

Tests were run on BDUs treated with Permethrin and amylopectin in the manner described, and the following synergistic results were uncovered.

EXAMPLE 1

Seven new nylon/cotton temperate BDUs (TBDUs), coat and trousers, were treated with amylopectin and Permethrin pursuant to the process above-described, and 50 laundry cycles were run. At the end of cycles 0 (control), 1, 10, 20, 30, 40, and 50, a pair of BDU coat and trousers was removed, the water extracted, and the residual Permetherin content determined by gas chromatographic analysis (GCA). The results are shown in FIG. 1 and Table 1. The same procedure was gone through again in a repeat trial marked "rept" in FIG. 1 and designated "#2" in Table 1. The resultant Permethren retention levels are indicated in values of mg. Permethren per square centimeter of material. In both of the trials involving treatment of the fabric with amylopectin, the Permethren retention level at the end of 50 cycles an integral multiple of the level of Permethrin in clothing that was not treated with amylopectin.

TABLE 1

(Impregnation of Amylopectin Treated TBDUs with Permethrin)

| | Field Laundry Cycles (values in mg/cm sq) | | | | | | |
|---|---|---|---|---|---|---|---|
| | 0 | 1 | 10 | 20 | 30 | 40 | 50 |
| No Amylopectin | 0.139 | 0.092 | 0.073 | 0.031 | 0.018 | 0.012 | 0.010 |
| Amylopectin | 0.132 | 0.138 | 0.101 | 0.082 | 0.069 | 0.058 | 0.048 |
| Amylopectin (#2) | 0.147 | 0.130 | 0.095 | 0.084 | 0.077 | 0.075 | 0.071 |

EXAMPLE 2

Figure 2:
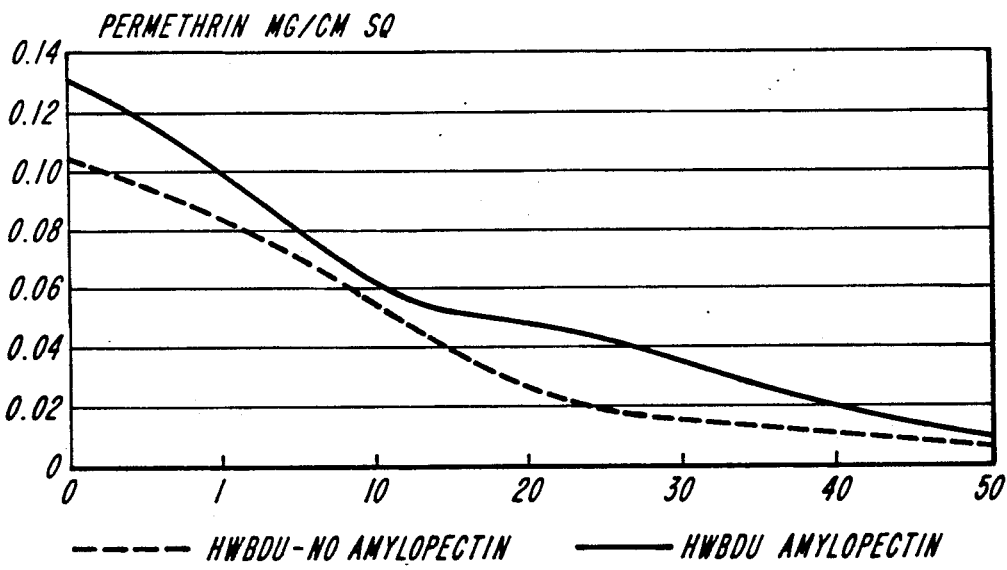
FIG. 2 is a graph showing Permethrin retention in Hot Weather (100% cotton) Battle Dress Uniforms in combination with amylopectin and without amylopectin.

Seven new 100% cotton hot water BDUs (HWBDUs), coat and trousers, were treated with amylopectin and Permethrin pursuant to the process above-described, and 50 laundry cycles were run. At the end of cycles 0 (control), 1, 10, 20, 30, 40, and 50, a pair of BDU coat and trousers was removed, its water extracted, and its residual Permethrin content determined by gas chromatographic analysis (GC). The results are shown in FIG. 2 and Table 2.

TABLE II (Impregnation of Amylopectin Treated HWBDUs with Permethrin)

| | Field Laundry Cycles (values in mg/cm sq) | | | | | | |
|---|---|---|---|---|---|---|---|
| | 0 | 1 | 10 | 20 | 30 | 40 | 50 |
| No Amylopectin | 0.104 | 0.087 | 0.054 | 0.022 | 0.014 | 0.010 | 0.006 |
| Amylopectin | 0.131 | 0.104 | 0.051 | 0.050 | 0.035 | 0.018 | 0.009 |

In view of the foregoing examples, it is apparent that the combination of amylopectin and Permethrin provides unexpectedly high retention of Permethrin through a substantial number of laundering cycles.

As previously stated, the order in which the amylopectin and Permethrin are applied does not appear to be critical, though it is suspected that wetting the fabric in the presence of the soluble starch may improve conditions by which the Permethrin bonds with the fabric. However, it is not presently known whether the Permethrin specifically bonds with the material. Moreover, it is not known at present whether the steam pressing is of critical effect, i.e. whether steam pressing melts or otherwise alters the structural characteristics of Permethrin, but is not believed to be necessary at the present time.

While a preferred embodiment of the invention has been described herein, it is to be understood by those skilled in the art that modifications ma be made therein without departing from the scope and spirit of the invention.

What is claimed is:

1. A method for retaining Permethrin in textiles, comprising the steps of:

placing the textiles in a predetermined liquid to allow the textiles to be wetted thereby;

adding amylopectin to the predetermined liquid permitting thereby the textiles to become exposed in solution to the amylopectin;

extracting the predetermined liquid from the textiles;

rolling the textiles tightly;

placing the tightly rolled textiles into a sealable bag;

pouring into the bag an amount of Permethrin and water no more than the maximum amount which may be totally absorbed by the tightly rolled textiles;

sealing the bag for a time selected to permit the rolled textiles to absorb the Permethrin; and removing the textiles from the bag after said time has elapsed.

2. The method of claim 1 wherein the textiles are clothing, the predetermined liquid is water, and wherein the step of placing the clothing in water comprises placing the clothing into a laundry machine and rinsing the clothing with clear water at one-hundred twenty (120) degrees Fahrenheit for a predetermined time.

3. The method of claim 2, wherein said predetermined time is thirty (30) seconds.

4. The method of claim 2, wherein the step of adding amylopectin to the water comprises applying amylopectin at a concentration of 0.75% for five minutes at 120 degrees Fahrenheit.

5. The method of claim 2 wherein the step of extracting water from the clothing comprises spinning the clothes to permit removal of water by centrifugal action.

6. The method of claim 2 wherein the step of extracting water from the clothing comprises steam-pressing the clothing.

7. A method providing enhanced retention of Permethrin in textiles over multiple laundry cycles of the textiles comprising the step of applying the Permethrin in combination with amylopectin to the textiles.

8. The method of claim 7, wherein the applying step includes applying said Permethrin and said amylopectin to the textiles sequentially in any or.

* * * * *